United States Patent [19]

Cullen et al.

[11] Patent Number: 5,187,301

[45] Date of Patent: * Feb. 16, 1993

[54] PREPARATION OF IMINODIACETONITRILE FROM GLYCOLONITRILE

[75] Inventors: Barry A. Cullen, Lyndeboro; Brian A. Parker, Nashua, both of N.H.

[73] Assignee: W. R. Grace & Co.-Conn., New York, N.Y.

[*] Notice: The portion of the term of this patent subsequent to Jul. 16, 2009 has been disclaimed.

[21] Appl. No.: 597,247

[22] Filed: Oct. 11, 1990

Related U.S. Application Data

[63] Continuation-in-part of Ser. No. 427,414, Oct. 26, 1989, abandoned.

[51] Int. Cl.$^5$ .............................................. C07C 253/30
[52] U.S. Cl. ..................................... 558/455; 558/346
[58] Field of Search ................................. 558/346, 455

[56] References Cited

U.S. PATENT DOCUMENTS

| | | | |
|---|---|---|---|
| 2,442,547 | 6/1948 | Mostek | 260/464 |
| 2,511,487 | 6/1950 | Thompson | 260/465.5 |
| 2,731,490 | 1/1956 | Barsky | 260/465.6 |
| 2,752,383 | 6/1956 | Belt | 260/465.6 |
| 2,794,044 | 5/1957 | Miller | 260/465.5 |
| 3,167,580 | 1/1965 | Saunders | 260/465.5 |
| 3,412,137 | 11/1968 | Stutts et al. | 260/465.5 |
| 3,904,668 | 9/1975 | Gaudette et al. | 260/465.5 A |
| 3,988,360 | 10/1976 | Gaudette et al. | 260/465.5 A |
| 4,543,215 | 9/1985 | Brunnmueller et al. | 260/465.5 |
| 4,661,614 | 4/1987 | Most et al. | 558/346 |
| 4,895,971 | 1/1990 | Su et al. | 558/346 |
| 4,948,909 | 8/1990 | Koeng et al. | 558/346 |

FOREIGN PATENT DOCUMENTS

| | | |
|---|---|---|
| 3242193 | 5/1984 | Fed. Rep. of Germany . |
| 746641 | 12/1932 | France . |
| 0068725 | 6/1978 | Japan . |
| 744675 | 2/1956 | United Kingdom . |

OTHER PUBLICATIONS

Eschweiler, Ann 278 (1894) pp. 232–243 (Translation of pp. 235–238 included).

*Primary Examiner*—Joseph Paul Brust
*Attorney, Agent, or Firm*—Kevin S. Lemack; William L. Baker

[57] ABSTRACT

A process for producing iminodiacetonitrile (IDAN) from glycolonitrile and ammonia or its salt is disclosed. In the batch process, pH is controlled with the addition of ammonia or suitable acids. In the continuous process, glycolonitrile and ammonia are reacted in near stoichiometric amounts at a temperature from about 90° C. to about 180° C.

11 Claims, 10 Drawing Sheets

PREPARATION OF IMINODIACETONITRILE FROM GLYCOLONITRILE

This application is a continuation-in-part of application Ser. No. 427,414, filed Oct. 26, 1989, now abandoned.

BACKGROUND OF THE INVENTION

1. Field of the Invention

This invention relates to the conversion of glycolonitrile to iminodiacetonitrile.

2. Description of the Prior Art

Numerous methods for preparing iminodiacetonitrile (IDAN) are disclosed in the prior art. For example, U.S. Pat. No. 2,511,487 to Thompson teaches reacting aminoacetonitrile with formaldehyde cyanhydrin at a temperature of about 50° C. to 150° C. in the absence of alkali.

U.S. Pat. No. 2,794,044 to Miller discloses reacting ammonia, formaldehyde and hydrogen cyanide in a molar ratio of 2:3:3 at a pH of 5.5 to 6.5 and a temperature of from about 0° C. to 50° C. for 10-24 hours.

U.S. Pat. No. 3,167,580 to Saunders, et. al. discloses reacting hydrogen cyanide, ammonia and formaldehyde while critically controlling the mixing of the reactants, the mole ratio of each of the reactants, the temperature and pH of the reaction, and the residence time of the reactants.

U.S. Pat. No. 3,412,137 to Stutts discloses preparing IDAN by reacting hexamethylenetetramine with about 6 molar equivalents of hydrogen cyanide in a buffered aqueous medium at a pH of from about 5 to 6.5 and a temperature of between about 0° and 75° C.

U.S. Pat. No. 4,661,614 to Most et. al. discloses preparing IDAN by reacting formaldehyde, hydrogen cyanide and a source of ammonia under substantially stoichiometric conditions at a temperature between about 30° C. and 65° C. and a pH between about 1.5 and 5.5.

However, each of the foregoing processes suffers from various drawbacks, such as the added burden of forming complex starting reactants, poor yield, critical reaction conditions, etc.

SUMMARY OF THE INVENTION

The problems of the prior art have been overcome by the instant invention, which provides a novel process for producing iminodiacetonitrile by reacting preformed glycolonitrile with an ammonia source.

It is therefore an object of the invention to provide a new and improved process for the production of iminodiacetonitrile.

It is a further object of the invention to provide a process of producing iminodiacetonitrile in high yield and low cost.

A still further object of the invention is to provide a process for producing iminodiacetonitrile from a stable intermediate and without the requirement for storing volatile and unstable HCN.

Another object of the invention is to provide a process for producing iminodiacetonitrile by an easily controlled reaction mechanism.

DETAILED DESCRIPTION OF THE INVENTION

On an industrial scale, the formation of IDAN from hydrogen cyanide, formaldehyde and ammonia requires purified, commercial grade hydrogen cyanide and formaldehyde in order to obtain product in high enough yield t be economically feasible. Purification of crude HCN and formaldehyde adds substantial cost and time to the IDAN production process.

Accordingly, the instant invention is directed to a process for preparing IDAN by reacting preformed glycolonitrile with an ammonia source. The glycolonitrile can be formed by optionally using crude reaction gases from an HCN reactor and a HCHO reactor as starting reactants without sacrificing reaction time or product yield. Specifically, crude (or purified) HCN and crude (or purified) formaldehyde are reacted to form glycolonitrile. This reaction removes heat in that it is exothermic, releasing approx. 10 Kcal./g. Mole. In addition, the glycolonitrile so produced is a stable, non-volatile product that can be stored at ambient temperature.

The reaction sequence is illustrated as follows:

$$HCN + CH_2O \rightarrow CH_2OHCN \quad (1)$$

$$2CH_2OHCN + NH_3 \rightarrow HN(CH_2CN)_2 + 2H_2O \quad (2)$$

In Reaction #1, glycolonitrile is formed in a process (either batch or continuous) by maintaining the pH of the formaldehyde above about 3, preferably in a range of about 5-7, most preferably about 5.5, with suitable acids and bases, such as acetic acid or sulfuric acid and sodium hydroxide or ammonia. It will be obvious to those skilled in the art that other acids and bases can be used for pH adjustment. The exact pH used will depend on the particular configuration of the equipment. The formaldehyde is then reacted with hydrogen cyanide in a temperature range of about 20°-80° C., preferably about 30° C. to form glycolonitrile.

Suitable sources of hydrogen cyanide and formaldehyde to form the glycolonitrile can comprise crude, unpurified product streams from hydrogen cyanide and formaldehyde production processes. For example, commercially available hydroge cyanide is produced primarily by the ammoxidation of methane, the reaction of ammonia and propane (alkane ammono-dehydrogenation), the ammoxidation of methanol, the dehydration of formamide, and the recovery of hydrogen cyanide as the by-product in the preparation of acrylonitrile by the ammoxidation of propylene. These commercial processes use ammonia as the nitrogen source or may have ammonia present as a by-product. This ammonia has previously been removed prior to recovering hydrogen cyanide, which removal resulted in substantial capital requirements, and increased chance of release of HCN to the environment.

To produce purified HCN, the off-gases stripped free of ammonia are scrubbed in a large absorption column and then distilled, adding significantly to both the danger of a release of HCN to the environment and t the capital requirements. Similarly, commercial grade formaldehyde is typically produced by the oxidative dehydrogenation of methanol over silver catalyst, or by the oxidation of methanol over a metal oxide catalyst. Each such process requires large absorption columns to recover formaldehyde.

Much of these recovery and purification costs can be eliminated by employing the crude, unpurified reaction product streams of a hydrogen cyanide and/or formaldehyde production process in producing glycolonitrile. Preferably, these unpurified streams are gaseous; the hydrogen cyanide stream comprising a gaseous mixture of hydrogen cyanide, oxides of carbon, water, and ammonia, and the formaldehyde stream comprising a gaseous mixture of formaldehyde, oxides of carbon and water.

If the source of HCN to form the glycolonitrile to produce IDAN is the off-gases from an HCN reactor, then ammonia may be present. If desired, this ammonia may be removed by either passing the crude HCN gases through an acid scrubber, as is well known to those skilled in the art, or neutralized with a suitable acid during the formation of glycolonitrile. The removal of ammonia results in ease in balancing reaction conditions.

Of course, suitable sources of hydrogen cyanide and formaldehyde also include purified hydrogen cyanide and/or purified formaldehyde.

The resulting glycolonitrile can, if desired, be stabilized by lowering the pH to less than about 4, preferably to about 2, with a suitable acid, such as sulfuric acid, phosphoric acid or other acid known to be suitable to those skilled in the art.

For formation of IDAN from glycolonitrile (Reaction #2), prepared from ammonia free HCN and either purified or crude formaldehyde in a batch process, the pH and temperature are controlled in order to realize excellent conversions of glycolonitrile to IDAN. The temperature of the glycolonitrile is adjusted to about 40°-150° C., preferably about 60°-110° C., most preferably about 90° C. An ammonium salt or salts of non-oxidizing acids with $pK_a$'s of less than about 5, which are not deleterious to the formation of IDAN, such as ammonium sulfate and/or acetate is added at a rate of about 0.01-0.5 M/M glycolonitrile, preferably about 0.17M/M to serve as a source of ammonia to produce IDAN. In addition, ammonia is added in a controlled manner to maintain the pH in the range of from about 3 to about 9, preferably in the range of from about 5 to about 7, most preferably in the range of from about 5.3 to about 6.3. The reduction in pH occurs because as ammonia is consumed from the ammonium salt, free acid is liberated. If insufficient ammonium salt is present the reaction rate is limited. This can be overcome with the addition of additional ammonium salt. Alternatively, controlled addition of a suitable acid will result in the formation of ammonium salt from the excess ammonia being added to maintain PH. Suitable acids include sulfuric, phosphoric, acetic, etc. The careful regulation of pH serves to control the amount of impurities generated and maximize the conversion to IDAN. The concentration of IDAN reaches a maximum after several minutes to several hours depending on the reaction temperature. At this time the demand for ammonia ceases and the pH of the reaction mass begins to rise. This is due to polymerization of the IDAN to a black intractable solid that liverates ammonia.

If IDAN is to be made from glycolonitrile that contains ammonia, as free ammonia and/or ammonium salt, the batch process as described above may be used, employing similar reaction conditions. It may be necessary to add a suitable acid to lower the pH to the desired operating range. Additional ammonium salt may or may not be required depending upon the concentration of ammonia and/or salt in the glycolonitrile. The amount of ammonia, and/or ammonium ion therein can be determined by suitable measurement.

In another embodiment of the present invention, glycolonitrile and ammonia and/or an ammonium salt or salts of non-oxidizing acids with $pK_1$'s of less than about 5, which are not deleterious to the formation of IDAN, are reacted in a continuous reactor in mole ratios of about 1.5-2.5:1, preferably in substantially stoichiometric mole ratios to form IDAN, without the necessity of controlling pH. Larger excesses of glycolonitrile can also be used, but are economically unattractive. Where the glycolonitrile used is formed from crude HCN gases such as from a conventional Andrussow HCN reactor, and from crude HCHO such as from conventional iron/molybdenum catalyzed methanol oxidation, the glycolonitrile solution comprises about 70–80 grams of $H_2O$ per mole of glycolonitrile. This glycolonitrile and 100% ammonia are reacted in a cascading continuous stirred tank reactor, tubular reactor or other suitable reactor at a temperature of from about 90° to about 180° C., preferably about 145° to about 175° C., most preferably about 165° C. The reaction may also be carried out at a pressure sufficient to keep the reacting mass from boiling, typically about 100–200 psig.

As the concentration of the reagents increases, corresponding, for example, to the use of commercial (100%) HCN and commercial (44%) HCHO, about 35–40 grams of $H_2O$ per mole of glycolonitrile are present. In such a case, a reaction temperature of from about 80° C. to about 160° C., preferably about 110° C. to about 155° C., most preferably about 135° C. is appropriate.

The mole ratio of glycolonitrile to ammonia is preferably about stoichiometric. Residence times are in the range of several seconds to several hours, depending on the reaction conditions employed. Preferably the conditions are such that residence times of about 30 seconds to about 4 minutes are achieved, more preferably about 1 minute to 2.5 minutes, most Preferably about 1 minute. Where the glycolonitrile has been acid stabilized, the most preferred residence time is about 2 minutes.

Because the conversion of glycolonitrile to IDAN is so efficient and few by-products are present, the reaction mass can be hydrolyzed in suitable acid or base to produce iminodiacetic acid (IDA) or its salts without prior removal of the IDAN from the process stream. IDA is the major commercial end product of IDAN.

The instant invention will be better understood by referring to the following specific but nonlimiting examples. It is understood that said invention is not limited by these examples which are offered merely as illustrations; it is also understood that modifications can be made without departing from the spirit and scope of the invention.

APPARATUS BATCH PROCESS

Figure 1:
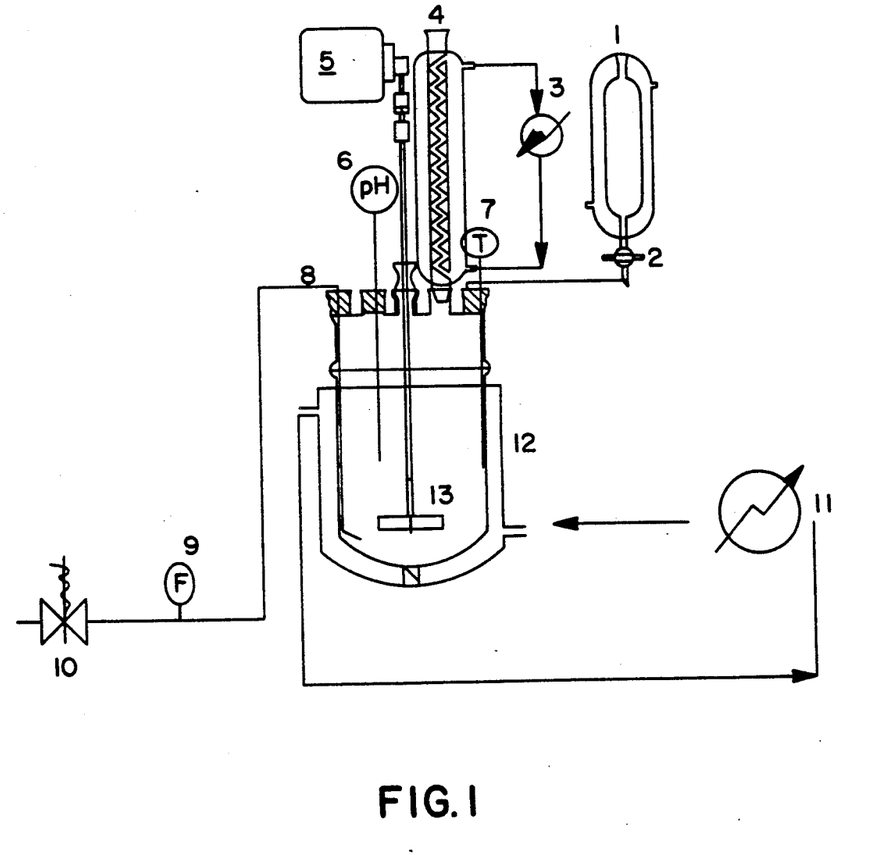
FIG. 1 illustrates laboratory apparatus used to carry out the batchwise embodiment of the present invention.

A 1 liter 5 necked jacketed resin kettle 12 with a bottom take-off valve is heated using a heat exchanger 11 and is equipped with an addition funnel 1 for acid, a solenoid coil 2 (110 V) which is connected to a relay switch on the titrator (not shown) to maintain pH control, a ¼" stainless steel cooling/heating coil (not shown) inserted into the kettle 12, stiring motor 5, glass stirring shaft with Teflon stirring blade 13, condenser 4, heat exchanger 3, resistance temperature device (RTD) 7, double junction Ingold 465-35-90-K9 combination pH electrode 6 and one ⅛" stainless steel tube 8 reaching to the bottom of the kettle 12 below the agitator. This apparatus was used to prepare IDAN by the "glycolonitrile batch process". The apparatus employed is shown in FIG. 1.

The pH control mechanism was designed so that a 110 V ASCO solenoid valve 10 controlled by a Radiometer pHM 26/Titrator II controlled the addition of anhydrous ammonia, according to the pH of the reaction mixture via the stainless steel dip leg 8. An ammonia flow meter 9 was also used.

Figure 8:
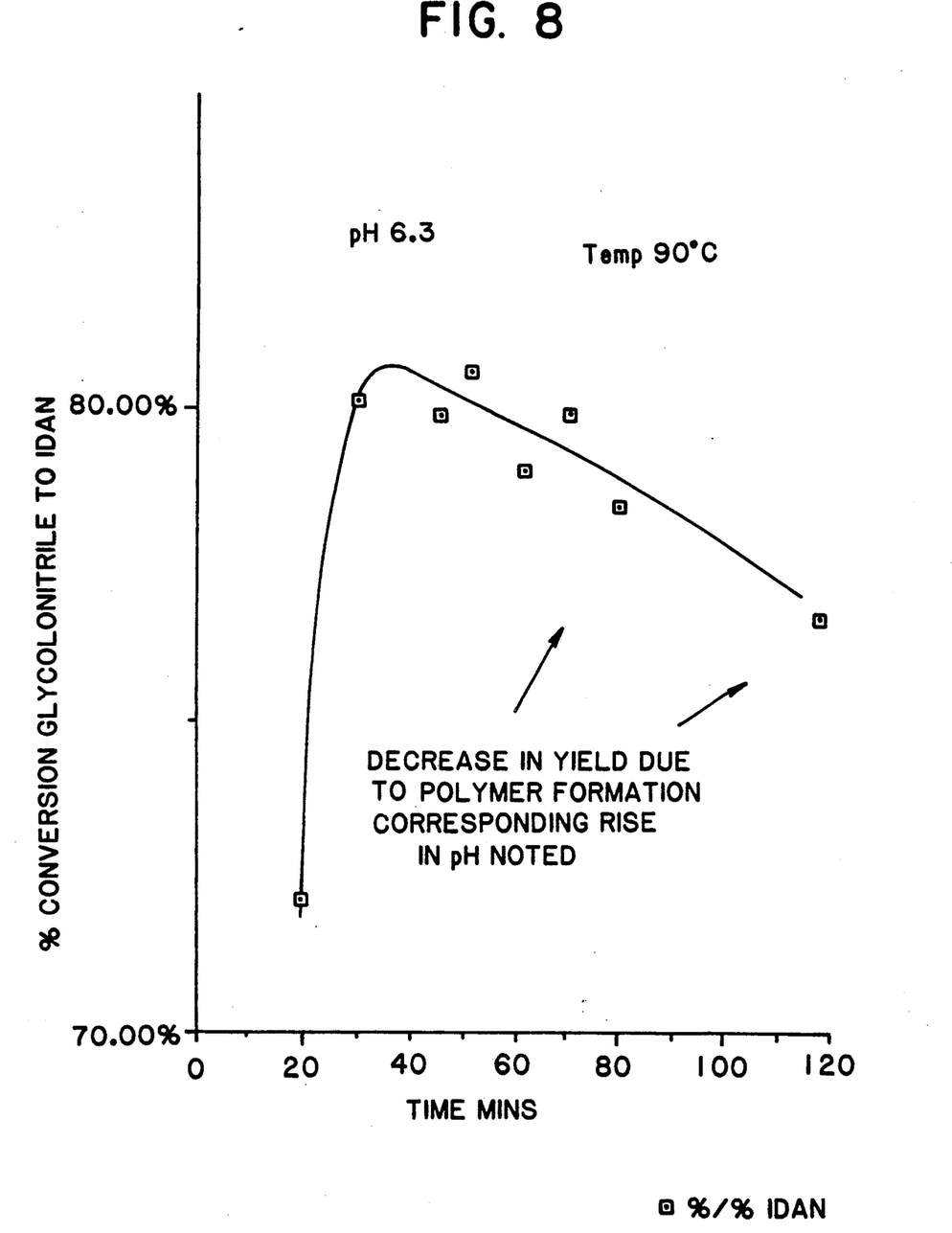
FIG. 8 is an exploded graph of the IDAN yield curve of FIG. 7.

The batch process Examples 1-5 are tabulated in Table I. The yield was found to eventually decrease and a corresponding rise in pH was noted when the reaction was carried out at high starting pH's (i.e., greater than 5.90). The decrease in yield is believed to be caused by the formation of polymer. FIG. 8 shows an exploded view of the yield of IDAN in accordance with Example 5.

TABLE 1

Batch process, conversion of glycolonitrile to IDAN, MBIDAN and glycinonitrile ½ SO4

| Experiment | Time Minutes | pH | % Conversion IDAN | glycinonitrile ½ so4 | MBIDAN |
|---|---|---|---|---|---|
| 1 | 0 | 5.30 | 0.00 | 0.00 | 0.00 |
|  | 15 | 5.30 | 18.50 | 1.48 | 2.21 |
|  | 33 | 5.30 | 37.05 | 0.94 | 0.00 |
|  | 45 | 5.30 | 47.95 | 0.95 | 0.00 |
|  | 60 | 5.30 | 54.60 | 0.83 | 1.85 |
|  | 75 | 5.30 | 61.07 | 0.80 | 0.00 |
|  | 90 | 5.30 | 68.68 | 0.77 | 0.00 |
|  | 105 | 5.30 | 68.68 | 0.77 | 0.00 |
|  | 120 | 5.30 | 72.27 | 0.81 | 1.72 |
|  | 136 | 5.30 | 74.08 | 0.91 | 0.00 |
|  | 150 | 5.30 | 75.42 | 0.87 | 0.00 |
|  | 165 | 5.30 | 76.01 | 0.94 | 1.38 |
| 2 | 0 | 5.55 | 0.00 | 0.00 | 0.00 |
|  | 11 | 5.55 | 12.00 | 1.83 | 1.69 |
|  | 21 | 5.55 | 22.36 | 0.98 | 3.60 |
|  | 34 | 5.55 | 33.97 | 0.83 | 4.37 |
|  | 56 | 5.55 | 48.04 | 0.61 | 4.15 |
|  | 70 | 5.55 | 53.18 | 0.71 | 4.26 |
|  | 90 | 5.55 | 60.90 | 0.58 | 4.21 |
|  | 105 | 5.55 | 65.68 | 0.61 | 3.93 |
|  | 125 | 5.55 | 68.56 | 0.65 | 3.73 |
|  | 145 | 5.55 | 69.27 | 0.72 | 3.62 |
|  | 165 | 5.55 | 71.85 | 0.65 | 3.71 |
|  | 190 | 5.55 | 74.14 | 0.88 | 2.71 |
|  | 210 | 5.55 | 75.15 | 0.84 | 2.30 |
|  | 240 | 5.55 | 76.78 | 0.88 | 2.49 |
| 3 | 0 | 5.90 | 0.00 | 0.00 | 0.00 |
|  | 15 | 5.90 | 38.63 | 2.36 | 3.32 |
|  | 25 | 5.90 | 52.88 | 1.86 | 4.48 |
|  | 35 | 5.90 | 63.39 | 1.57 | 4.68 |
|  | 45 | 5.90 | 69.12 | 1.57 | 4.51 |
|  | 61 | 5.90 | 74.70 | 1.47 | 4.09 |
|  | 77 | 5.90 | 77.11 | 1.49 | 4.07 |
|  | 91 | 5.90 | 78.86 | 1.44 | 3.32 |
|  | 105 | 5.90 | 78.86 | 1.34 | 2.24 |
|  | 120 | 5.90 | 78.80 | 1.40 | 2.57 |
|  | 155 | 5.94 | 78.95 | 1.41 | 1.65 |
|  | 180 | 6.04 | 75.89 | 1.87 | 1.63 |
| 4 | 0 | 6.05 | 0.00 | 0.00 | 0.00 |
|  | 10 | 6.05 | 25.18 | 2.81 | 1.00 |
|  | 20 | 6.05 | 43.71 | 1.82 | 2.66 |
|  | 30 | 6.05 | 54.60 | 1.60 | 2.93 |
|  | 50 | 6.05 | 66.57 | 1.47 | 2.27 |
|  | 70 | 6.05 | 73.18 | 1.41 | 1.99 |
|  | 95 | 6.05 | 74.79 | 1.53 | 1.58 |
|  | 120 | 6.05 | 77.73 | 1.67 | 1.24 |
|  | 150 | 6.10 | 77.32 | 1.82 | 1.83 |
|  | 167 | 6.13 | 76.69 | 1.90 | 0.86 |
| 5 | 0 | 6.30 | 0.00 | 0.00 | 0.00 |
|  | 10 | 6.30 | 56.95 | 6.09 | 1.63 |
|  | 20 | 6.30 | 72.12 | 4.70 | 1.60 |
|  | 30 | 6.30 | 80.11 | 4.02 | 1.83 |
|  | 45 | 6.30 | 79.90 | 3.56 | 1.41 |
|  | 51 | 6.35 | 80.58 | 3.31 | 1.52 |
|  | 61 | 6.45 | 79.01 | 3.22 | 1.47 |
|  | 70 | 6.55 | 79.90 | 3.22 | 1.33 |
|  | 80 | 6.62 | 78.44 | 3.18 | 1.16 |
|  | 118 | 6.76 | 76.57 | 3.45 | 0.89 |

EXAMPLE 1

Glycolonitrile was prepared by reacting the equivalent of 1.00 mole of $CH_2O$ (37%) with 1.00 mole of 99.5% HCN at approx. 30° C. The pH of the $CH_2O$ was first adjusted to approx. 5.5 with acetic acid and sodium hydroxide. The resultant glycolonitrile solution was then stabilized with sulfuric acid by lowering the pH to 2.

An equivalent of 3.422 moles of the acid stabilized glycolonitrile was then added to the resin kettle. Steam heated the contents of the kettle to 90° C. and this temperature was then maintained by heating and cooling as necessary. Once the temperature stabilized, an equivalent of 0.570 moles of $(NH_4)_2SO_4$ was added to the resin kettle to simulate glycolontrile prepared at a pH of approx. 5.50 from an HCN reactor off gas stream containing $NH_3$. Immediately the Titrator II was turned on and periodic additions of $NH_3$ maintained the temperature compensated pH at 5.30 (within +/−pH 0.02). Samples were withdrawn at regular time intervals and analyzed by HPLC for glycinonitrile, glycolonitrile, methylene glycinonitrile trimer (MGN), IDAN, nitrilotriacetonitrile (NTAN) and methylene bis iminodiacetonitrile (MBIDAN) concentrations.

Figure 3:
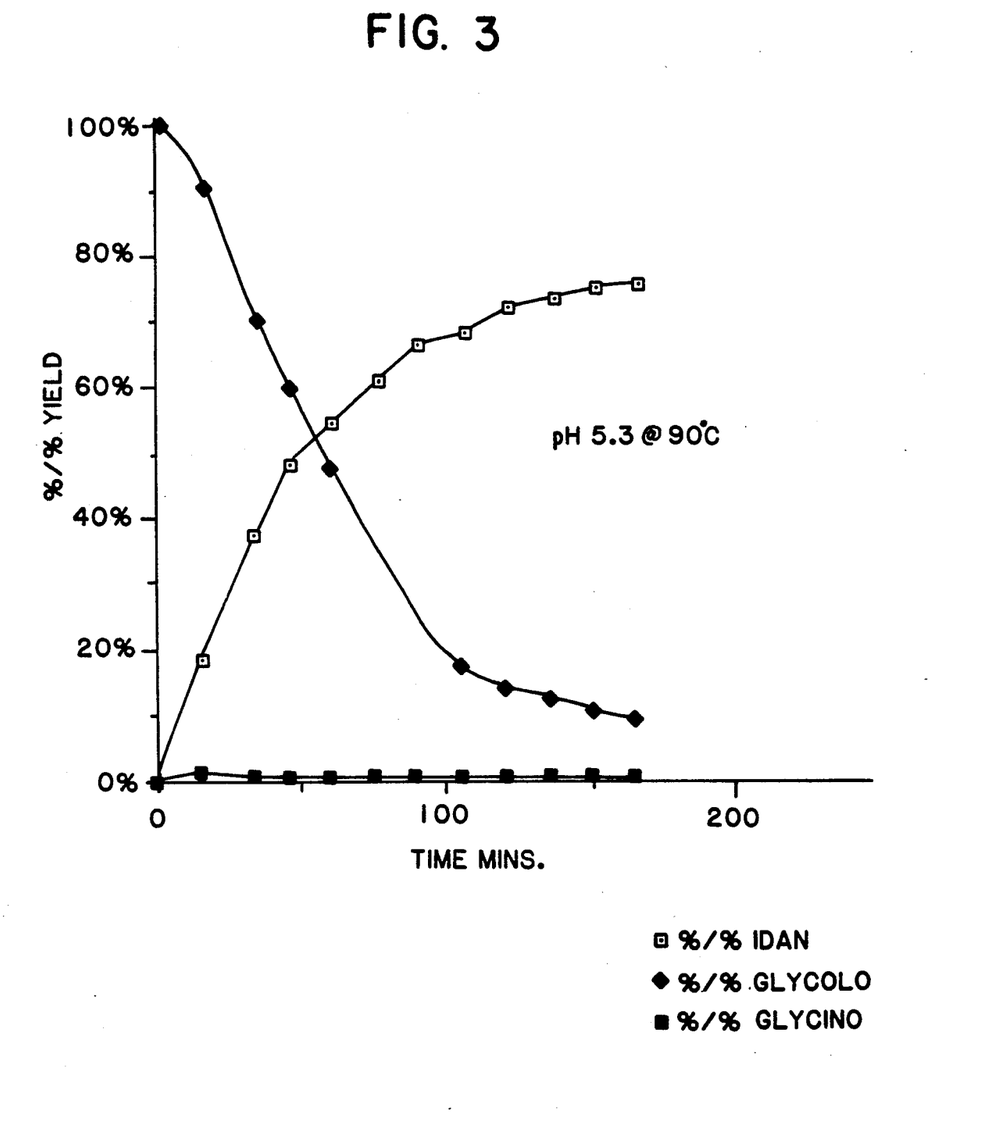
FIGS. 3-7 are graphs of the yield of IDAN and glycinonitrile and the conversion of glycolonitrile at various PH's.

The reaction initially proceeded very rigorously and appeared to be complete after 1 hour 30 minutes. The graph in FIG. 3 was generated as a result.

EXAMPLE 2

Figure 4:
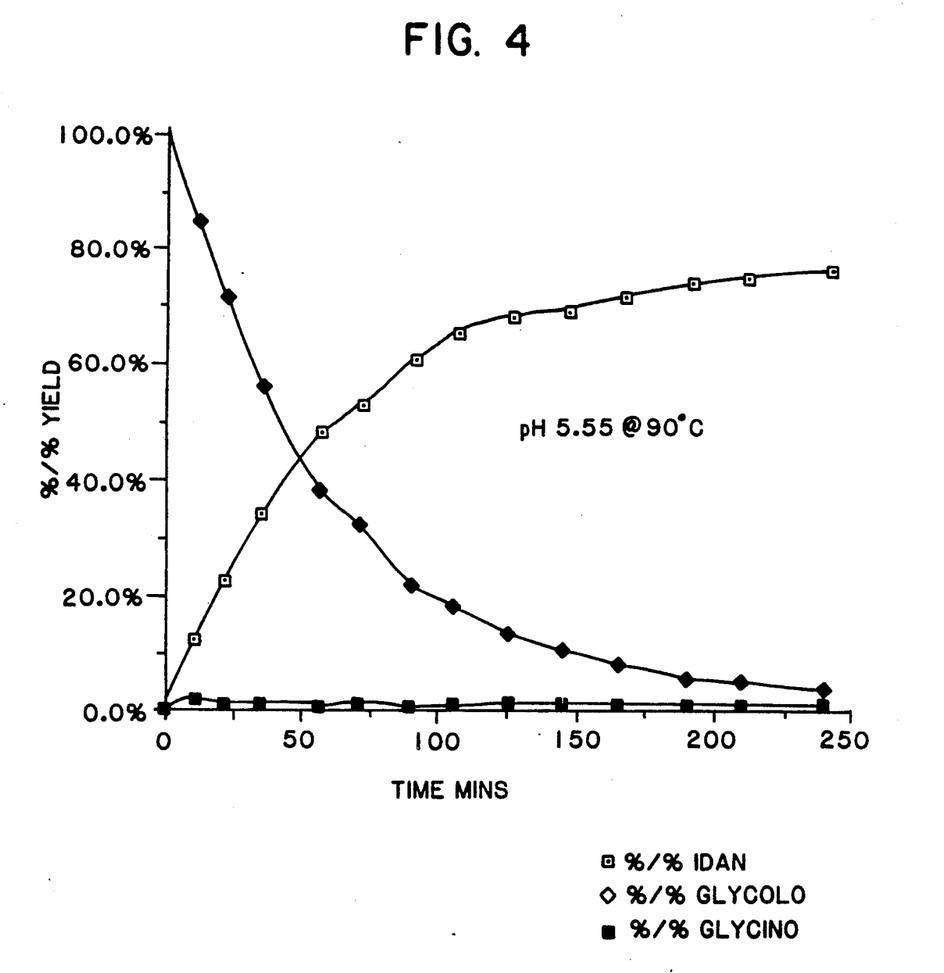

As Example 1 except the pH was maintained at 5.55. The graph in FIG. 4 was generated as a result.

EXAMPLE 3

Figure 5:
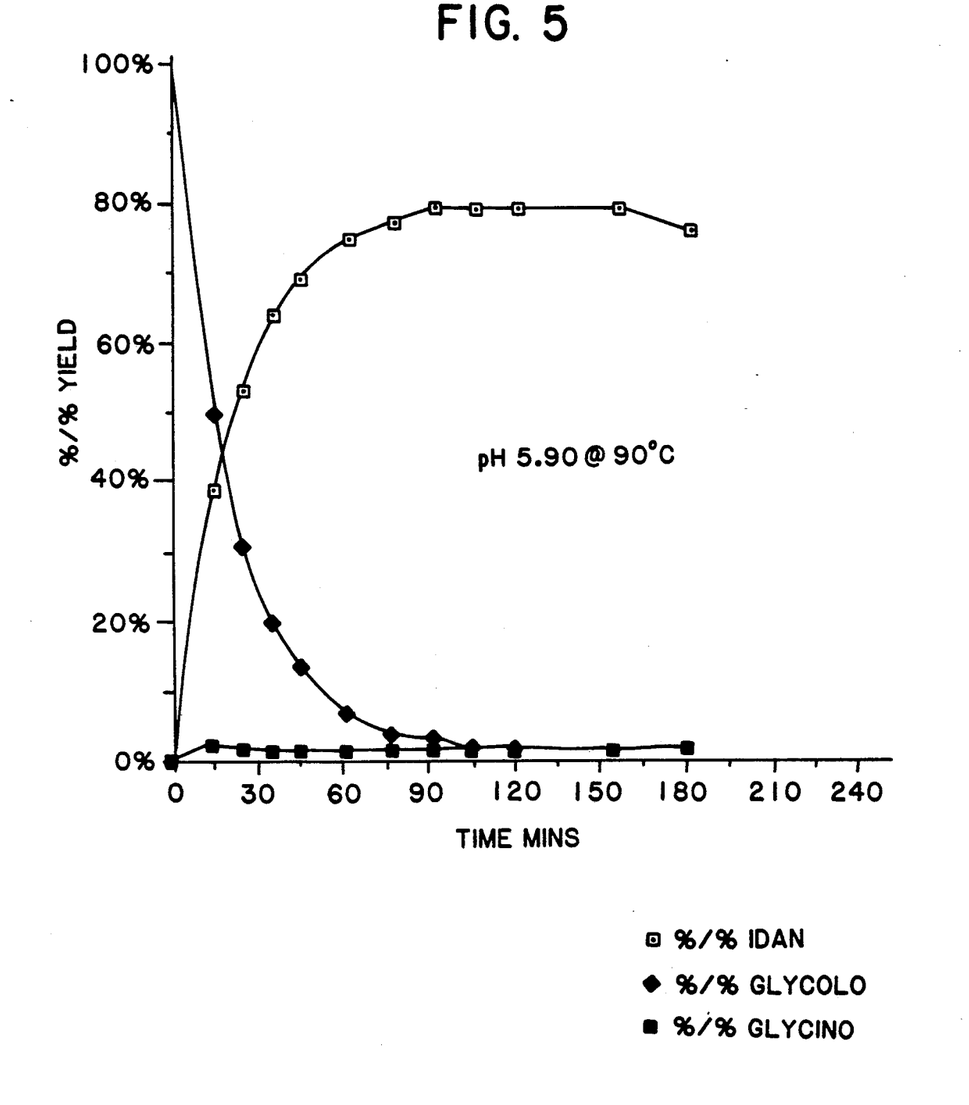

As Example 1 except the pH was maintained at 5.90. The graph in FIG. 5 was generated as a result.

EXAMPLE 4

Figure 6:
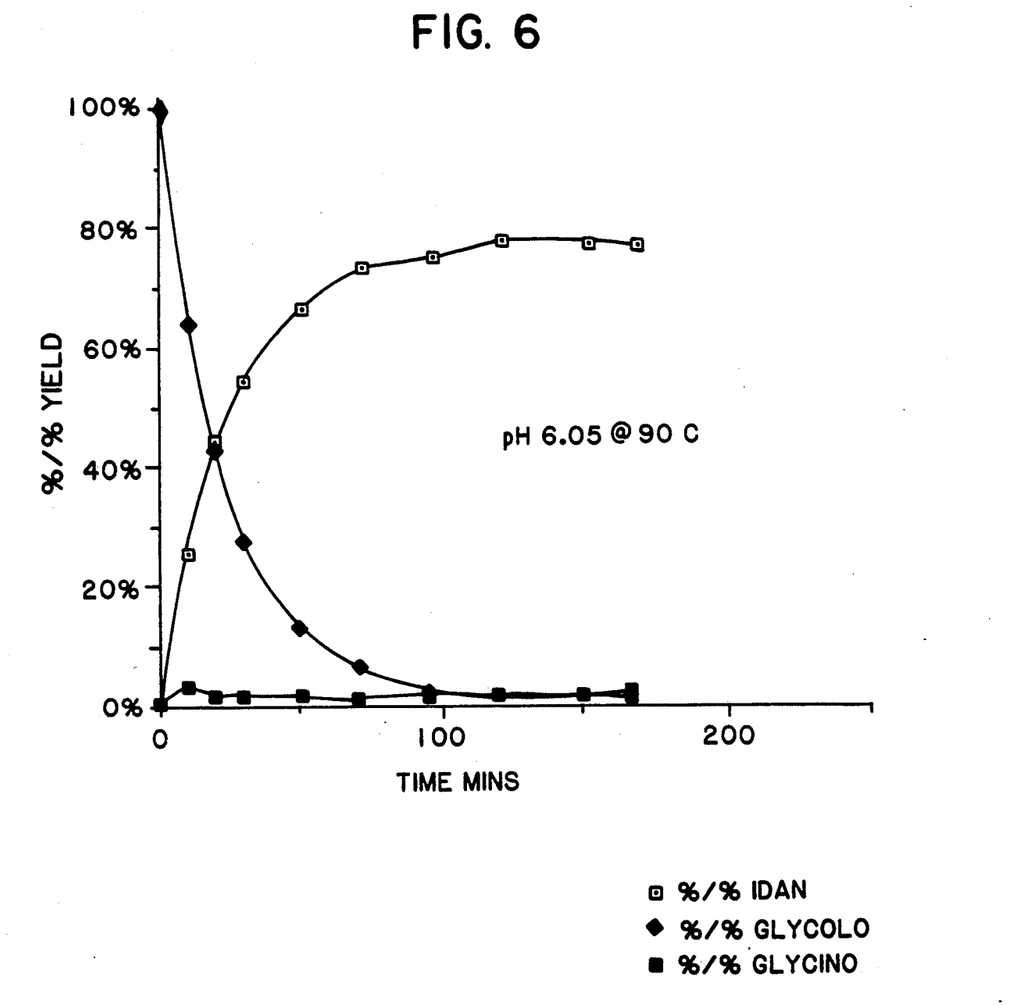

As Example 1 except the pH was maintained at 6.05. The graph in FIG. 6 was generated as a result.

EXAMPLE 5

Figure 7:
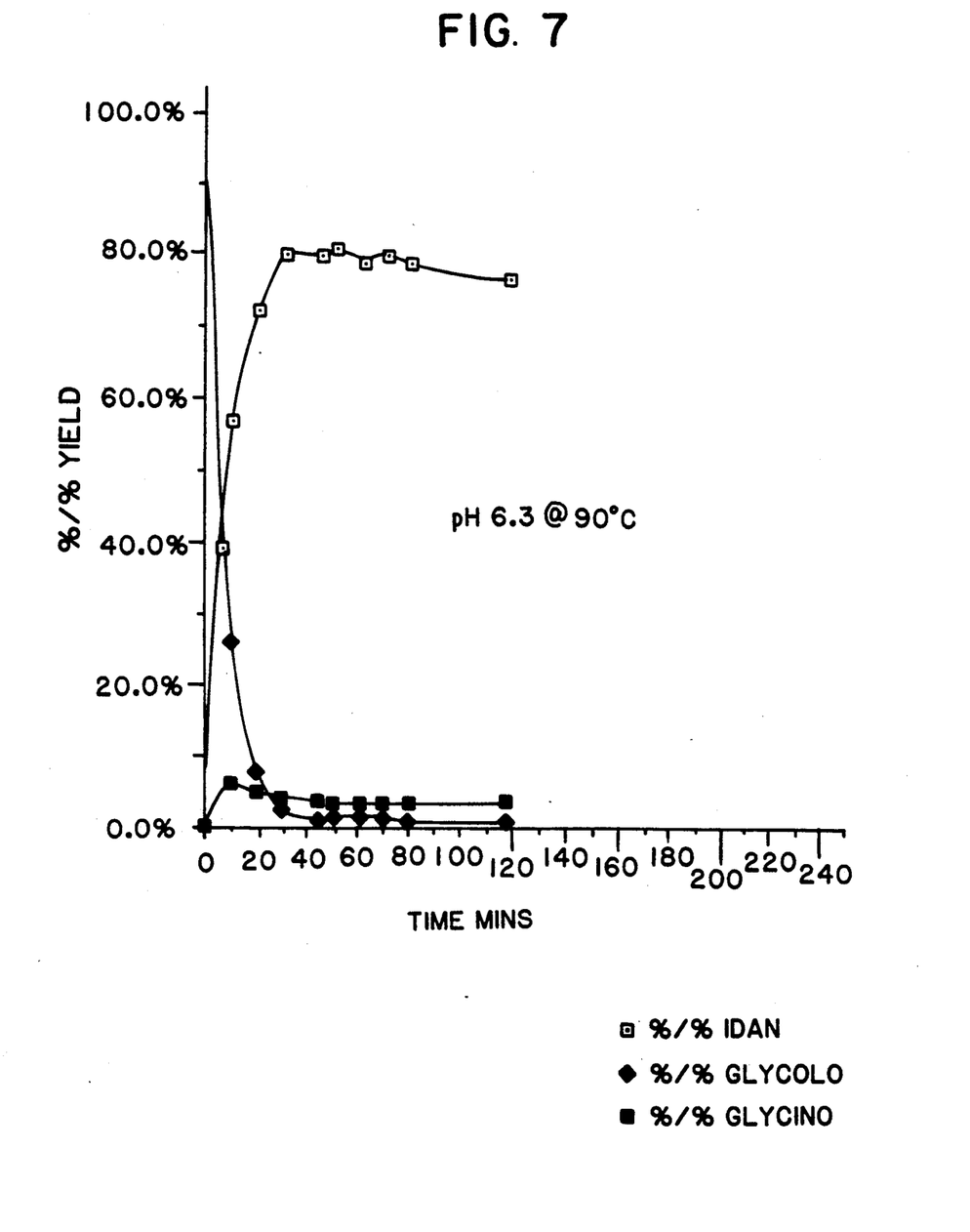

As Example 1 except the pH was maintained at 6.30. The graph in FIG. 7 was generated as a result. FIG. 8 is an exploded view of the IDAN yield curve of FIG. 7. It demonstrates the formation of intractable polymer at high operating pH's and long residence (retention) times, which results in decreases in IDAN yield and increases in reaction pH.

EXAMPLE 6

As in Example 1 except the pH was maintained at 5.85 and the temperature was held at 70° C. Crystals were isolated from the reaction mass. A yield of 81.71% was attained. During the reaction MBIDAN, NTAN and glycinonitrile calculated as [$(H_2NCH_2CN)_2SO_4$]- were found to be the major by-products at concentrations of ≦0.2%, ≦0.7% and ≦0.9%, respectively.

APPARATUS CONTINUOUS PROCESS

Figure 2A:
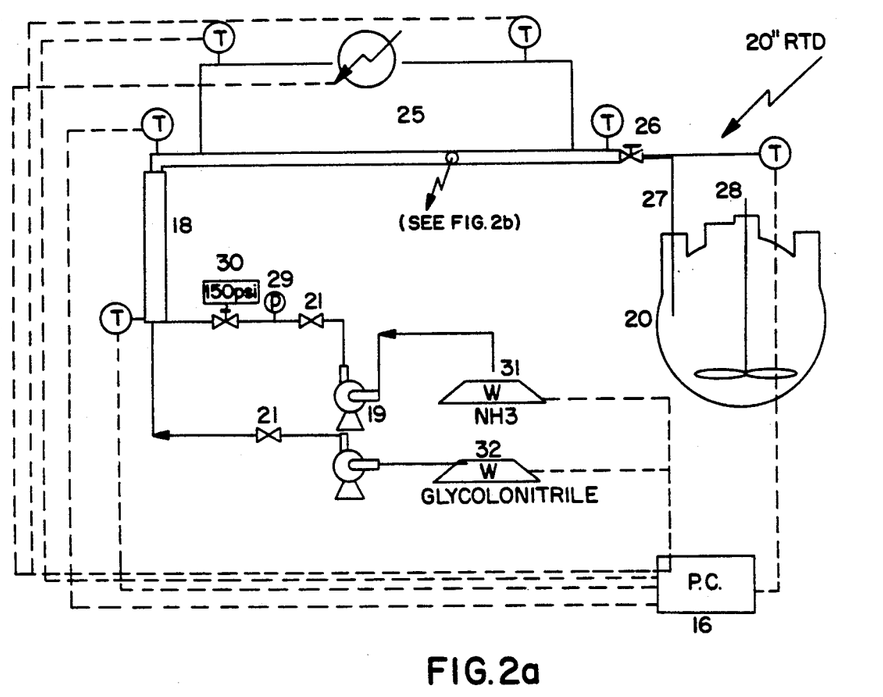
FIG. 2 illustrates laboratory apparatus used to carry out the continuous embodiment of the present invention.
Figure 2B:
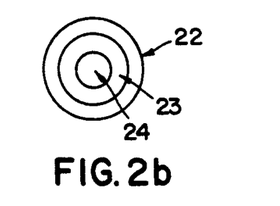

A process controller 16 was used to control the reaction and to gather data for the continuous process. By use of a software package, experimental control and data acquisition were easily achieved. The physical set-up of the process is shown in FIG. 2.

A 4 Kg balance 31 and a 4 Kg balance 32 were used to weigh NH₃ and glycolonitrile reactants, respectively. The tube reactor 25 consisted of ¼" stainless steel tubes which carried raw materials from their appropriate reservoirs to the mouth of a six stage ¼" static mixer 18. To avoid cavitation in the NH₃ pump head 19, a jacketed 3 liter reservoir 20 was pressurized with compressed air to 15 p.s.i. The reservoir 20 was equipped with a ¼" reactor eluent take off tube 27, and a glass stirring rod 28 having a Teflon stirring blade. Twenty psi Nupro check valves 21 were placed at the outlets of each pump head. A 0-500 p.s.i. gauge 29 is positioned after the check valve 21 for the NH₃ Pump, followed by a 500 p.s.i.g. pressure relief valve 30. The pump heads had maximum pumping rates of approx. 10 mls/minute for ammonia and approx. 20 mls/minute for glycolonitrile, and were driven by a 0-120 strokes/minute drive. The heat exchanger/reactor 25 consisted of a tube within a tube (3 concentric tubes of differing diameters) all materials being stainless steel. The outer tubing 22 was ⅜" in diameter and was used to carry the oil to regulate the temperature of the reactants. The middle tubing 23 was ⅜" in diameter and contained the reaction mixture. A Tescom 250 psi back pressure regulator 26 attached to the outlet of this tube maintained the pressure of the contents at a 100 psi. The tubing 24 was ¼" in diameter and accommodated an ⅛" R.T.D. This inner tubing was filled with Dow Corning high vacuum grease to ensure quick response of the R.T.D. upon repositioning. The overall effect of this "tube in a tube in a tube" facilitates better heat transfer to the reactants because of the relatively larger surface area available to them. The heating oil was delivered to the heat exchanger via ¼" copper tubing. It was recirculated at 250 mls per minute. The temperature of the oil bath was controlled with +1° C. of the set point by the software.

Under extreme conditions, that is, where residence times and temperatures longer or higher than those necessary to achieve maximum conversions to IDAN were employed, intractable polymer is formed. This is evident from the lower mass balances calculated for the tube, and eventual plugging of the tube with a black insoluble material.

GENERAL METHOD I

To prepare IDAN by the continuous tube reactor method, 52% -53% glycolonitrile and 28% NH₃ (total added water to simulate crude feed streams from both conventional HCHO and HCN reactors) were pumped through the tube. Once the desired ratio of flow between both raw materials was achieved, residence times in the tube reactor were changed by varying the pump drive speed. This normally involved little or no adjustment of the individual pump heads resulting in short tube equilibration times. The pumps on the pumping mechanism were previously synchronized so that a homogeneous mixture of reactants evolved from the static mixer shown in FIG. 2. The eluent from the tube was gathered periodically and analyzed by liquid chromatography (L.C.)

EXAMPLE 7

The General Method I described above was employed whereby the tube temperature was maintained at 100°-110° C. The initial residence time studies were 1 minute. The conversion to IDAN from glycolonitrile was found to be 66.3% by L.C.

The motor speed was decreased so that a residence time of 2 minutes could be attained. For this residence time conversion of glycolnitrile to IDAN was found to be 77.3%.

EXAMPLE 8

As in General Method I, whereby the residence time was 1 minute and the temperature was maintained at 140°-150° C. Conversion to IDAN was found to be 88.53% based on glycolonitrile. The eluent from the tube was gathered over a period of 1 hour and a crop of crystals was isolated by cooling followed by filtration in a 78.5% yield. L.C. analysis of the crystals revealed that the product was 100% IDAN.

EXAMPLE 9

As in General Method I above, whereby the residence time was 3 minutes and the temperature was 160°-170° C. The % conversion to IDAN based on glycolonitrile was found to be 86.1%. Glycolonitrile and glycinonitrile calculated as [$(H_2CH_2CN)_2SO_4$] were found in the reaction mass at 0.55% and 1.7%, respectively.

EXAMPLE 10

As in Example 9, whereby the glycolonitrile had been stabilized by the addition of 4.08×10 moles of H₂SO₄ per mole of glycolonitrile. 76.1% of the glycolonitrile as determined by L.C. was converted to IDAN.

EXAMPLE 11

As in Example 9, whereby the glycolonitrile had been stabilized by the addition of 16.3×10⁻³ moles of H₂SO₄ per mole of glycolonitrile. 69.2% of the glycolonitrile as determined by L.C. was converted to IDAN.

EXAMPLE 12

As in General Method I described above, whereby the residence time was 4 minutes and the temperature was maintained at 160°-170° C. The % conversion to IDAN based on the glycolonitrile was found to be 78.7% as determined by L.C.

EXAMPLE 13

As in Example 12, whereby the glycolonitrile had been stabilized by the addition of $4.08 \times 10^{-3}$ moles of concentrated H per mole of glycolonitrile. 73.5% of the glycolonitrile as determined by L.C. was converted to IDAN.

EXAMPLE 14

As in Example 12, whereby the glycolonitrile had been stabilized by the addition of $8.16 \times 10^{-3}$ moles of H per mole of glycolonitrile. 75.9% of the glycolonitrile as determined by L.C. was converted to IDAN.

EXAMPLE 15

As in Example 12, whereby the glycolonitrile had been stabilized by the addition of $16.3 \times 10^{-3}$ moles of H per mole of glycolonitrile. 81.1% of the glycolonitrile as determined by L.C. was converted to IDAN.

EXAMPLE 16

Figure 9:
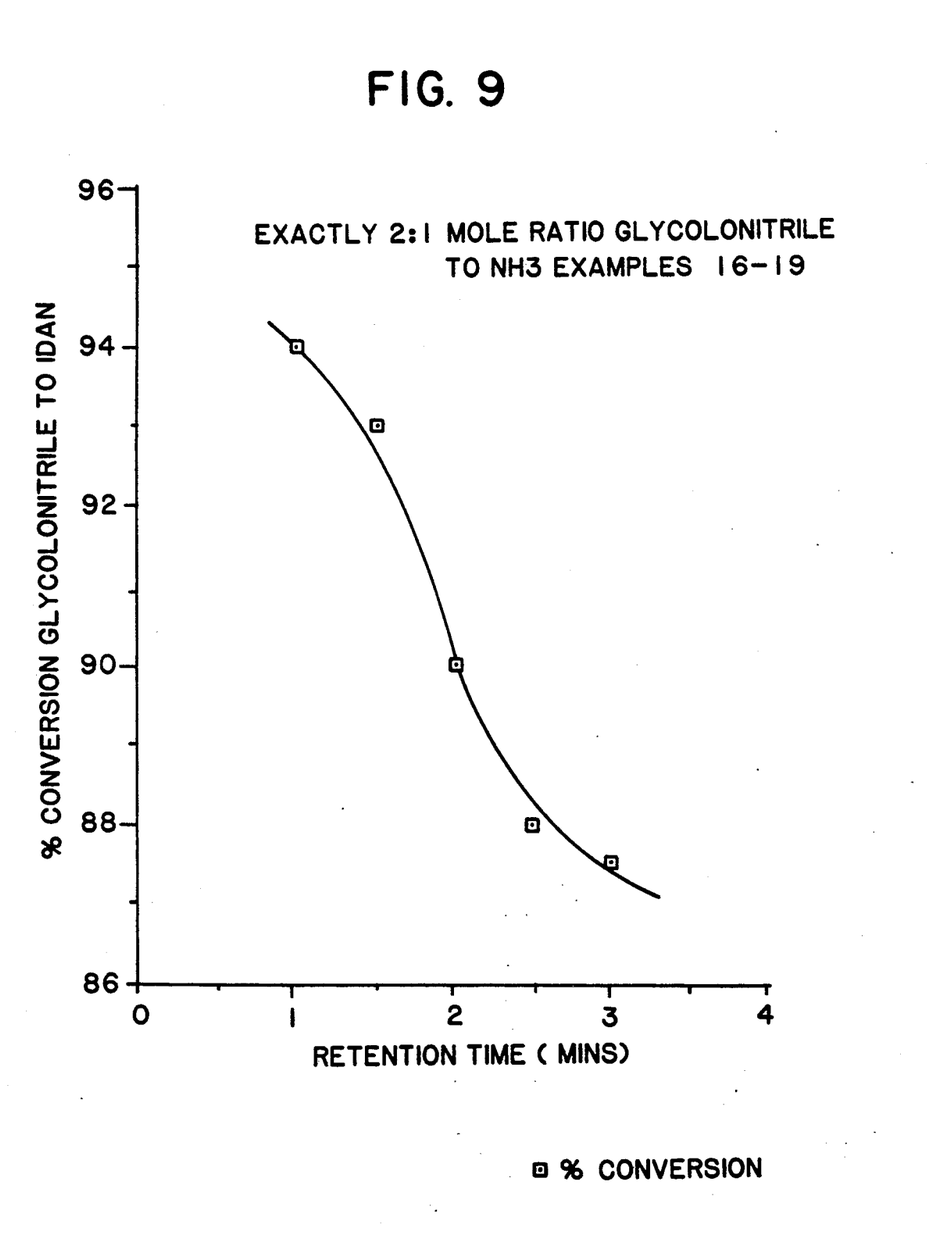
FIGS. 9-10 are plots of residence time vs. % conversion of glycolonitrile to IDAN

As in General Method I, whereby the residence time was 1 minute and the temperature was maintained at 165° C. The conversion to IDAN was 94.0% based on the glycolonitrile as determined by L.C. See FIG. 9.

EXAMPLE 17

As in Example 16 whereby the residence time was 1.5 minutes. The conversion to IDAN was found to be 92.4% based on the glycolonitrile as determined by L.C. See FIG. 9.

EXAMPLE 18

As in Example 16 whereby the residence time was 2.0 minutes. The conversion to IDAN was found to be 90.1% based on the glycolonitrile as determined by L.C. See FIG. 9.

EXAMPLE 19

As in Example 16, whereby the residence time was 2.5 minutes The conversion to IDAN was found to be 89.3% based on the glycolonitrile as determined by L.C. See FIG. 9.

EXAMPLE 20

As in General Method I whereby the glycolonitrile had been stabilized by the addition of $4.08 \times 10^{-3}$ moles of phosphoric acid/mole of glycolonitrile, a residence time of 1.0 minute and a temperature of 165° C. were employed. The conversion of glycolonitrile to IDAN was found to be 91.0% as determined by L.C.

EXAMPLE 21

As in Example 20, with a residence time of 1.5 minutes and a temperature of 165° C. The conversion of glycolonitrile to IDAN was found to be 94.2% as determined by L.C.

EXAMPLE 22

As in Example 20, with a residence time of 2.0 minutes and a temperature of 165° C. The conversion of glycolonitrile to IDAN was found to be 93.7% as determined by L.C.

EXAMPLE 23

As in Example 20, with a residence time of 2.5 minutes and a temperature of 165° C. The conversion of glycolonitrile to IDAN was found to be 91.7% as determined by L.C.

EXAMPLE 24

As in Example 20, with a residence time of 3.5 minutes and a temperature of 165° C. The conversion of glycolonitrile to IDAN was found to be 83.6% as determined by L.C.

EXAMPLE 25

Figure 10:
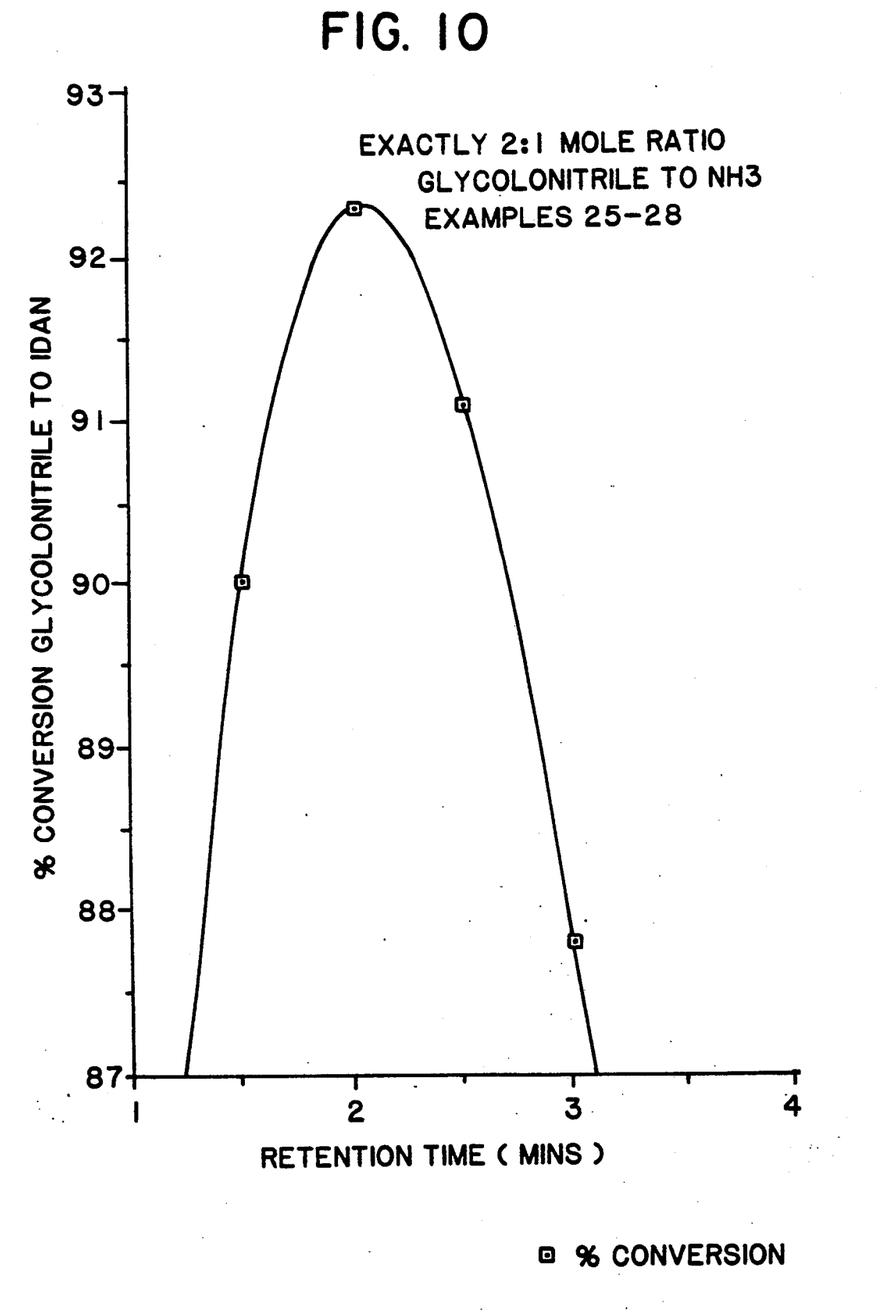

As in General Method I whereby the glycolonitrile had been stabilized by the addition of $8.16 \times 10^{-3}$ moles of phosphoric acid/mole of glycolonitrile, and a residence time of 1.5 minutes and a temperature of 165° C. were employed. The conversion of glycolonitrile to IDAN was found to be 90.0% as determined by L.C. See FIG. 10.

EXAMPLE 26

As in Example 25, with a residence time of 2.0 minutes and a temperature of 165° C. The conversion of glycolonitrile to IDAN was found to be 92.3% as determined by L.C. See FIG. 10.

EXAMPLE 27

As in Example 25, with a residence time of 2.5 minutes and a temperature of 165° C. The conversion of glycolonitrile to IDAN was found to be 91.1% as determined by L.C. See FIG. 10.

EXAMPLE 28

As in Example 25, with a residence time of 3.0 minutes and a temperature of 165° C. The conversion of glycolonitrile to IDAN was found to be 87.8% as determined by L.C. See FIG. 10.

EXAMPLE 29

As in General Method I whereby the glycolonitrile had been stabilized by the addition of $16.3 \times 10^{-3}$ moles of Phosphoric acid/mole of glycolonitrile, and a residence time of 1.5 minutes and a temperature of 165° C. were employed. The conversion of glycolonitrile to IDAN was found to be 87.0% as determined by L.C.

EXAMPLE 30

As in Example 29, with a residence time of 2.0 minutes and a temperature of 165° C. The conversion of glycolonitrile to IDAN was found to be 86.7% as determined by L.C.

EXAMPLE 31

As in Example 29, with a residence time of 2.5 minutes and a temperature of 165° C. The conversion of glycolonitrile to IDAN was found to be 85.5% as determined by L.C.

GENERAL METHOD II

General Method I was carried out, except that 59% -60% glycolonitrile and 100% $NH_3$ (total added water to simulate feed streams from commercially available 44% HCHO and approximately 100% HCN reactors) were pumped through the tube.

EXAMPLE 32

As in General Method II whereby a residence time of 1.0 minute and a temperature of 145° C. were employed. The conversion of glycolonitrile to IDAN was found to be 91.6% as determined by L.C.

EXAMPLE 33

As in General Method II whereby a residence time of 1.0 minute and a temperature of 135° C. were employed. The conversion of glycolonitrile to IDAN was found to be 87.0% as determined by L.C.

EXAMPLE 34

As in General Method II whereby a residence time of 1.5 minutes and a temperature of 135° C. were employed. The conversion of glycolonitrile to IDAN was found to be 90.0% as determined by L.C.

EXAMPLE 35

As in General Method II whereby a residence time of 2.5 minutes and a temperature of 135° C. were employed. The conversion of glycolonitrile to IDAN was found to be 88.6% as determined by L.C.

We claim:

1. A batchwise process for forming iminodiacetonitrile, comprising reacting preformed glycolonitrile with ammonia, ammonium slat not deleterious to the formation of said iminodiacetonitrile, or a mixture of ammonia and said ammonium salt, said ammonia, ammonium salt or mixture being added to aid glycolonitrile in a mole ratio of glycolonitrile to ammonia moiety of about 1.5-2.5:1 and at a rate sufficient to maintain he pH during the reaction in a range of from about 5 to about 7 while maintaining a reaction temperature of about 40° C. to about 150° C.

2. The process of claim 1 wherein said pH is maintained in a range from about 5.3 to about 6.3.

3. The process of claim 1 wherein said temperature is about 60°-110° C.

4. The process of claim 1 wherein said temperature is about 90° C.

5. The process of claim 1 wherein said glycolonitrile, prior to reaction with said ammonia, ammonium salt or mixture, has been stabilized to a pH below about 4.

6. A continuous process for forming iminodiacetonitrile, comprising continuously reacting preformed glycolonitrile and ammonia, ammionia salt not deleterious to the formation of said iminodiacetonitrile, or a mixture of ammonia and said ammonia slat, in a substantially stoichiometric mole ratio in a temperature range of from about 90° C. to about 180° C. without pH control.

7. The process of claim 6 wherein said temperature range is from about 145° C. to about 175° C.

8. The process of claim 6 wherein said temperature is about 165° C.

9. A continuous process for forming iminodiacetonitrile, comprising continuously reacting about 58 to 62% preformed glycolonitrile and ammonia, ammonium salt not deleterious to the formation of said iminodiacetonitrile, or a mixture of ammonia and said ammonium salt, in a substantially stoichiometric mole ratio in a tempera range of from about 80° c. to about 160° C. without pH control.

10. The process of claim 9 wherein said temperature range is from about 110° C. to about 155° C.

11. The process of claim 9 wherein said temperature is about 135° C.

* * * * *